United States Patent [19]  [11] Patent Number: 5,354,297
Avitall  [45] Date of Patent: Oct. 11, 1994

[54] BIPLANAR DEFLECTABLE CATHETER FOR ARRHYTHMOGENIC TISSUE ABLATION

[76] Inventor: Boaz Avitall, 4868 N. Ardmore Ave., Milwaukee, Wis. 53217

[21] Appl. No.: 909,867

[22] Filed: Jul. 7, 1992

Related U.S. Application Data

[63] Continuation-in-part of Ser. No. 835,553, Feb. 14, 1992, abandoned.

[51] Int. Cl.$^5$ .......................... A61B 5/04; A61N 1/05
[52] U.S. Cl. ..................................... 606/45; 128/772; 128/642; 607/122
[58] Field of Search ................ 128/639, 642, 784–786, 128/790, 772; 606/45, 46, 47, 48, 49, 53, 280–282; 604/53, 280–282; 607/115, 119, 122, 72

[56] References Cited

U.S. PATENT DOCUMENTS

| | | | |
|---|---|---|---|
| 4,522,212 | 6/1985 | Gelinas et al. | 128/786 X |
| 4,638,802 | 1/1987 | Okada | 606/47 |
| 4,641,649 | 2/1987 | Walinsky et al. | |
| 4,660,571 | 4/1987 | Hess et al. | |
| 4,677,990 | 7/1987 | Neubauer | 128/786 |
| 4,682,596 | 7/1987 | Bales et al. | |
| 4,699,147 | 10/1987 | Chilson et al. | 128/642 |
| 4,785,815 | 11/1988 | Cohen | |
| 4,869,248 | 9/1989 | Narula | 128/784 X |
| 4,882,777 | 11/1989 | Narula | 128/786 X |
| 4,920,980 | 5/1990 | Jackowski | 128/786 |
| 4,922,912 | 5/1990 | Watanabe | 128/786 X |
| 4,960,134 | 10/1990 | Webster, Jr. | 128/786 |
| 5,078,717 | 1/1992 | Parins et al. | 606/48 |
| 5,117,828 | 6/1992 | Metzger et al. | 128/784 |

Primary Examiner—Lee S. Cohen
Assistant Examiner—Samuel Gilbert
Attorney, Agent, or Firm—Haugen and Nikolai

[57] ABSTRACT

A cardiac arrhythmia ablation catheter has a highly flexible tubular distal catheter section for entering and exploring the walls of any cardiac chamber which, in turn, has a distal tip equipped with an electrode system, which may have a specialized shape, for mapping and ablating tissue and a dual-wire biplanar control system for enabling and controlling the movement of the distal catheter section and tip in any direction in a manner such that the distal tip is capable of accessing any point on the wall of the chamber entered. The dual-wire biplanar control system includes a vertical deflection control wire operable to deflect the distal tip of the catheter in a controlled manner a plane substantially parallel to the longitudinal axis of the tubular catheter and a lateral deflection control wire operable to deflect the distal tip of the catheter in a controlled manner in a plane substantially perpendicular to the longitudinal axis of the tubular catheter.

20 Claims, 4 Drawing Sheets

BIPLANAR DEFLECTABLE CATHETER FOR ARRHYTHMOGENIC TISSUE ABLATION

CROSS-REFERENCE TO RELATED APPLICATION

This patent application is a continuation-in-part of co-pending application Ser. No. 07/835,553, filed Feb. 14, 1992 now abandoned.

Reference is made to applications Ser. Nos. 07/840,026 and 07/840,162 of common inventorship. Both of these cross-referenced applications also are directed to improved catheters.

BACKGROUND OF THE INVENTION

1. Field of the Invention

The present invention is directed generally to an improved catheter apparatus for use in the field of cardiac arrhythmia ablation. In particular, the invention involves the use of a biplanar deflection system which greatly increases the maneuverability of the catheter tip in the lateral plane generally perpendicular to that of the disposition of the main catheter tube. This allows the operator to direct the tip of the catheter in multiple directions and maneuver the catheter as close as possible to the site of the arrhythmogenic tissue of interest to accomplish effective ablation.

2. Discussion of the Related Art

Normal cardiac pacing, in a healthy heart, is controlled by a special structure known as the sinoatrial node (SA node). This is the natural pacemaker of the heart and is a specialized tissue located within the muscle walls of the right atrium. The SA node provides impulses which dominate the inherent or natural rhythmic contractions of the heart atria and the ventricles. This dominance or control involves the transmission of ionic impulses through cardiac conduction pathways in the atria and the ventricles which cause the heart to contract and relax in an orderly sequence at a rate dictated by the SA node. This sequence ensures that blood flow to the systemic circulation or the pulmonary system will be maximized with each ventricular contraction. The SA node has its own inherent rate which can be modified by signals from the nervous system. In response to excitement, physical activity, etc., the sympathetic and parasympathetic nervous systems react to modify the rate.

A depolarization impulse begins with the SA node and spreads as an electrical wave from its location in the right atrium across to the left atrium and down toward the transition zone between the atrium and the ventricles where another node, known as the atrioventricular (A-V) node or junction, is located. This impulse conducts through the A-V node in a slower fashion and continues to a common pathway known as the Bundle of His between the right and left ventricles, then into multiple paths called right and left bundle branches, each bundle branch supplying one ventricle. These bundle branches then divide into an extensive network of finer paths of conducting tissue which spread from the inner to the outer surfaces of the heart and which are referred to as the Purkinje fibers. These fibers feed the depolarization impulse into all portions of the ventricular myocardium.

As long as this system is intact, impulses are transmitted normally and cardiac rhythm is maintained. The natural impulse or current flow in the cardiac conduction system, however, may be interrupted or altered by congenital defect, disease or injury which can cause the formation of scar tissue. When a sufficiently severe injury or a congenital defect is present in the cardiac conductive pathways or in the ventricular myocardium, the electrical impulses are not transmitted normally and rhythmic disturbances known as cardiac arrhythmias can occur. With respect to such disturbances, the term bradycardia is used to describe an abnormal slowing of the cardiac contractions and the term tachycardia is used to describe abnormally rapid heart action. While either of these conditions can endanger the life of the patient, tachycardia is the more serious, particularly in patients having underlying heart disease.

Ventricular tachycardia and other ventricular arrhythmias have been treated with a number of drugs such as lidocaine, quinidine and procainamide. In cases of excessive sympathetic nervous activity or adrenal secretion, Beta blocking drugs have been used. In cases where drug therapy has been ineffective in preventing tachyarrhythmias, certain surgical procedures have been used to ablate the arrhythmogenic tissue either from the atrium or the ventricles. This procedure involves extensive surgery in which an incision through the pericardium and heart muscle is made locate the arrhythmogenic tissue, which is then frozen or surgically removed to be replaced by scar tissue.

Because open-heart surgery is a high risk procedure which requires a prolonged period of hospitalization and recuperation, a less traumatic solution is needed. In response, catheters of various types have been devised and used for diagnosing and treating a number of cardiac abnormalities to avoid the trauma of open-heart surgery. For example, as a method for resolving atherosclerotic plaque build up, stenotic lesions are now routinely opened by the use of balloon angioplasty. In this procedure, a balloon carrying catheter is navigated through the patient's vascular system to the location of the stenosis. The balloon is inflated by fluid injected through a lumen of the catheter to apply pressure to the walls of the clogged vessel, thereby opening it.

Catheter devices have also been used to locate and ablate cardiac conduction pathways. One such device is shown in U.S. Pat. No. 4,785,815, in which a catheter tube carries at its distal end at least one electrode for sensing membrane potentials within the heart, together with a heating device for ablating at least a portion of the pathway located by the sensing device. Another thermal ablation catheter for microtransection or macrotransection of conduction pathways within the heart, which uses a resistive heating element at its distal end for highly localized treatment, is illustrated and described in U.S. Pat. No. 4,869,248. These devices are generally effective once the ablating element is properly positioned at the localized area of interest. A catheter device tip of the class described has also been developed which employs a single, handle-operated deflection wire. Such a device is disclosed in U.S. Pat. No. 4,960,134.

Electrophysiological catheter ablation procedures often have been hampered by the inability of the operator to maneuver the catheter tip to the precise location of the arrhythmogenic tissue. This is primarily a result of the limited maneuverability of the catheter tube itself. The catheter tube must have sufficient strength and stiffness to be guided through the vascular system to the vicinity of the tissue of interest. This construction does not allow the degree of flexibility at the tip of the catheter needed to perform intricate multidirectional manipulations in the highly localized areas involved. Available catheters, even catheters with single deflection wire control, are characterized by inadequate control of fine movements and have tips that can be deflected only in planes parallel to the main catheter tube. They lack the ability for controlled lateral movement in planes perpendicular to that of the main catheter tube within the atria or the ventricles.

Most present cardiac tissue ablation procedures involve the use of radio frequency (RF) electrical current transmitted to the tissue via a catheter which is positioned as closely as possible to the arrhythmogenic site within the atria or ventricles. Radio frequency electrical current heats the tissue surrounding the catheter, creating a discrete dense lesion. In order for the patient to be cured of the arrhythmia, the lesion must be created in the area from which the arrhythmia originates. Improvement in the maneuverability of such devices could optimize precise positioning of the catheter prior to ablation.

SUMMARY OF THE INVENTION

The present invention provides a new catheter design which endows the catheter tip with increased flexibility. The increased flexibility involves the incorporation of a biplanar deflection system which allows control of the lateral movements of the catheter tip.

The catheter system of the present invention includes an elongated flexible tubular catheter having a proximal end, a distal end and a central lumen extending therebetween. The outside diameter of the tubular catheter is such that it can be routed through the vascular system of a patient and into the heart chamber of interest to be treated. This is typically 7–8 French in size. The distal portion of the main tubular section of the catheter in the present invention includes a flexible distal tip section fabricated from a highly flexible reinforced polymer tubing material, preferably polyethylene, which is connected to the main catheter tube. A portion of this flexible tubing extends inside the distal end of the main tubing section of the catheter.

The flexible distal tip section of one embodiment includes a cylindrical metallic tip electrode which is preferably of noble metal such as platinum and, in one successful embodiment, is 4 mm long and 3 mm in diameter. One or more additional electrodes, preferably 2 or 3 ring electrodes, are serially spaced proximally from the tip electrode, typically starting 2 mm behind the tip electrode and spaced about 2 mm apart.

In an alternate embodiment, the electrode-carrying catheter tip section may have a "memory" in terms of a predetermined fixed shape which is re-assumed outside the conveying catheter lumen. This may be accomplished by using a flexible but memoried material which may be a plastic or a metallic material such as a nickel titanium alloy known commonly as nitinol. In this manner, specialized shapes to access and address specific internal cardiac areas may be created in mapping/ablation electroded tips which assume custom designed shapes when deployed. The mapping/ablation tips generally employ a plurality of serially spaced, separately connected electrodes in any desired configuration or number. The electrodes are typically up to 4 mm in length with 3 mm separations. The pre-shaped tips may be designed or readily adapted to operate with the tip deflection system of the invention, keeping in mind limitations of a fixed shape.

All of the electrodes are individually connected to an input/output device, typically an electrical phono jack type connector, by thin low resistance wire conductors. The phono jack or other connector is attached to the handle. The electrodes can be connected to a recording system which measures and displays cardiac depolarization potentials sensed within the involved cardiac chamber. This system can be used to map the earliest activation time indicating the most desirable location for tissue ablation. The tip electrode (or any other electrode) can be used for both electrical mapping when connected to the recording equipment and to deliver the ablation energy when connected to an energy source.

The system also includes a pair of control wires, a vertical deflection control wire and a lateral deflection control wire. The vertical deflection wire controls the deflection of the tip in a plane parallel to the main catheter tube (vertical deflection). It includes a wire, preferably of stainless steel, connected to a T-shaped pin, also preferably of stainless steel. The T-shaped pin is anchored or imbedded in the flexible distal section spaced about 3–4 mm from the tip electrode and provides the anchor for the vertical deflection wire.

The deflection of the tip is achieved by operating a longitudinally movable portion provided in the handle section which causes the wire to tense and relax. Tension in the vertical deflection wire inherently causes the tip to deflect since the insertion position of this wire is off center and in the side of the flexible portion of the catheter. This wire is threaded in the central lumen through the main body of the catheter to the handle.

Lateral deflection and control is achieved using highly torqueable wire which is flexible only at the end and which is inserted into the flexible deflectable distal portion of the catheter. The proximal portion of this wire is significantly more rigid. It is threaded through the length of the rigid portion of the catheter and extends out of the catheter tubing through a radial opening at a point spaced distally from the handle and is connected to a hand-operated rotatable lateral adjustment control knob mounted from the catheter handle at a fixed distance therefrom. The distal end of this wire is fixed to, usually by soldering, the tip electrode. Rotation of the knob left or right transmits rotational torque to the catheter tip. When the distal catheter tip is vertically deflected, the application of torque through this wire causes the distal tip to deflect laterally. The knob system is configured so that the knob can rotate freely when it is pushed down and locks in position when released. The rotational knob system is further designed to allow only a predetermined, limited number of rotations, possibly 5 or 6, to each side to prevent the operator from over-rotating the wire which could result in a fracture thereof.

Vertical deflection of the catheter tube is accomplished by longitudinal movement of the handle. Lateral movement control is achieved by turning the rotation knob in the desired direction. Adjustment of the rotation knob and the handle allow precise positioning of the tip in the heart.

Continuous recording of electrical activity while the catheter tip is in any deflection or rotational position is possible since the tip electrode is connected to a conductive wire which is connected to the phono connector. The tip is further connected to a source of radio frequency (RF) electrical current for ablation.

BRIEF DESCRIPTION OF THE DRAWINGS

In the drawings, wherein like numerals are utilized to designate like parts.

DETAILED DESCRIPTION

Figures 1, 2:
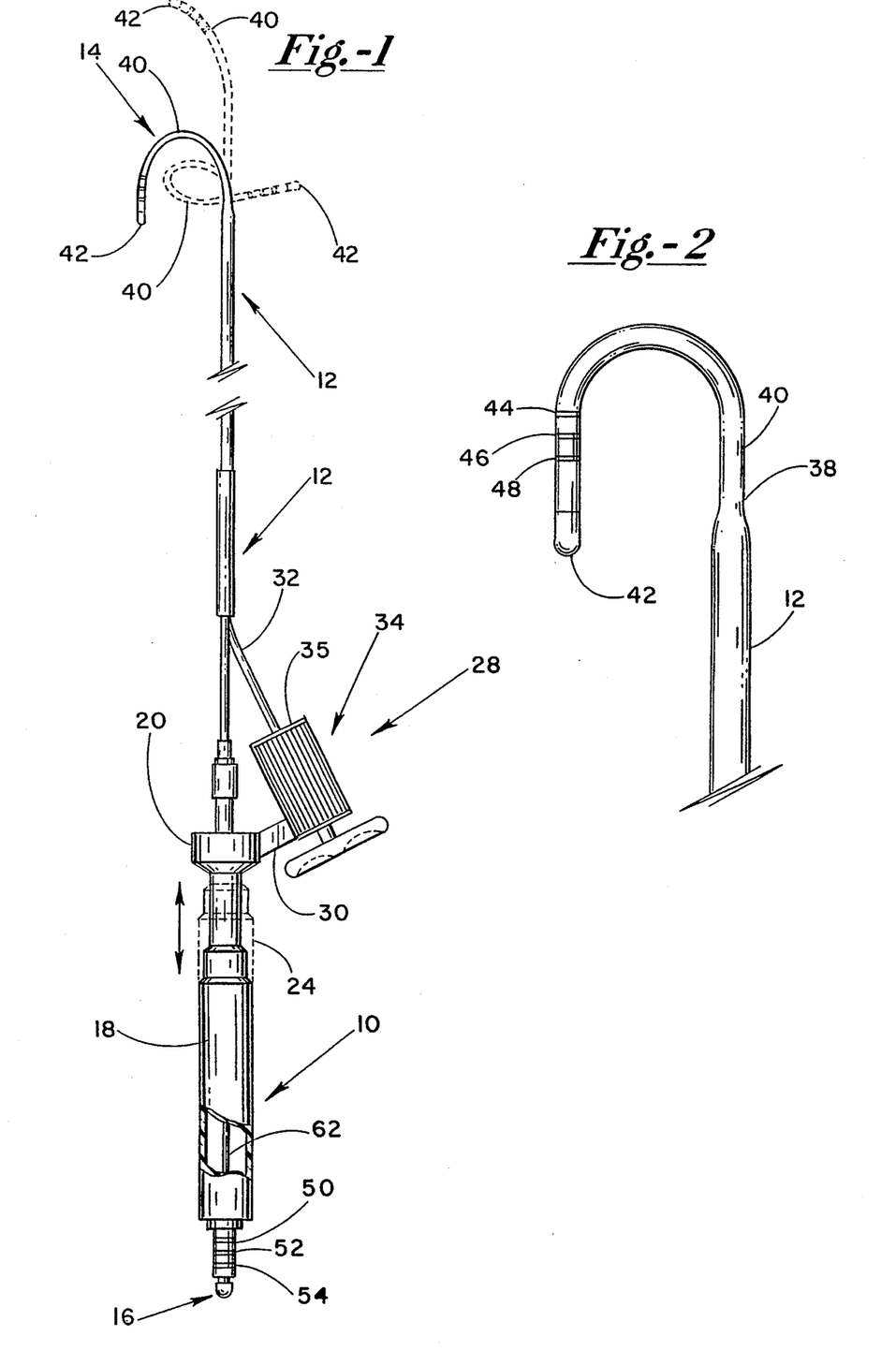
FIG. 1 is a side view of the catheter system showing the flexible tip segment in various positions.
FIG. 2 is an enlarged fragmentary view depicting the flexible tip section of FIG. 1.

The biplanar tissue ablation catheter system is shown in FIG. 1 and includes a handle portion shown generally at 10, a central, relatively rigid tubular section 12, and a flexible distal maneuverable tip section 14. The central section 12 is shown broken as it depicts the long main body of the catheter.

The handle portion further includes an electrical jack-type plug-in device 16 having multiple input/output pick off points associated with conductors discussed below. An outer hand grip section 18 in the handle portion is made freely adjustable for a distance along the longitudinal axis of the handle relative to the inner tubular handle section 20. The distance of adjustment is further illustrated in phantom at 24. The handle includes a hand-operated rotatable lateral tip deflection control knob shown generally at 28, is fixed in position spaced from the handle by a mounting member 30 and connected with the Central tubular section by a tubular member 32. The knob itself 34 is longitudinally and rotationally adjustable and will be more fully described in conjunction with FIG. 4, below. Relatively small tubular members 32 are threaded through the main catheter tube 12 which, in turn, is connected with the slightly necked-down flexible, maneuverable distal tip section 14 by a transition 38. The flexible tip section further includes a proximal segment of flexible reinforced polymer catheter tubing 40 which connects the distal end of the main catheter tube 12 and an electrode-containing platinum catheter tip system 42. The tubing segment 40 may be of any convenient length, typically about 4 to 8 centimeters, depending on the desired use. The tubing segment may be of any biologically compatible, relatively inert polymeric material having the requisite strength and flexibility together with the ability to be incorporated with other catheter materials may be reinforced with materials to achieve needed characteristics. The thin, relatively flexible reinforced tubing generally has an ID of about 3 mm or less.

Figures 3, 4:
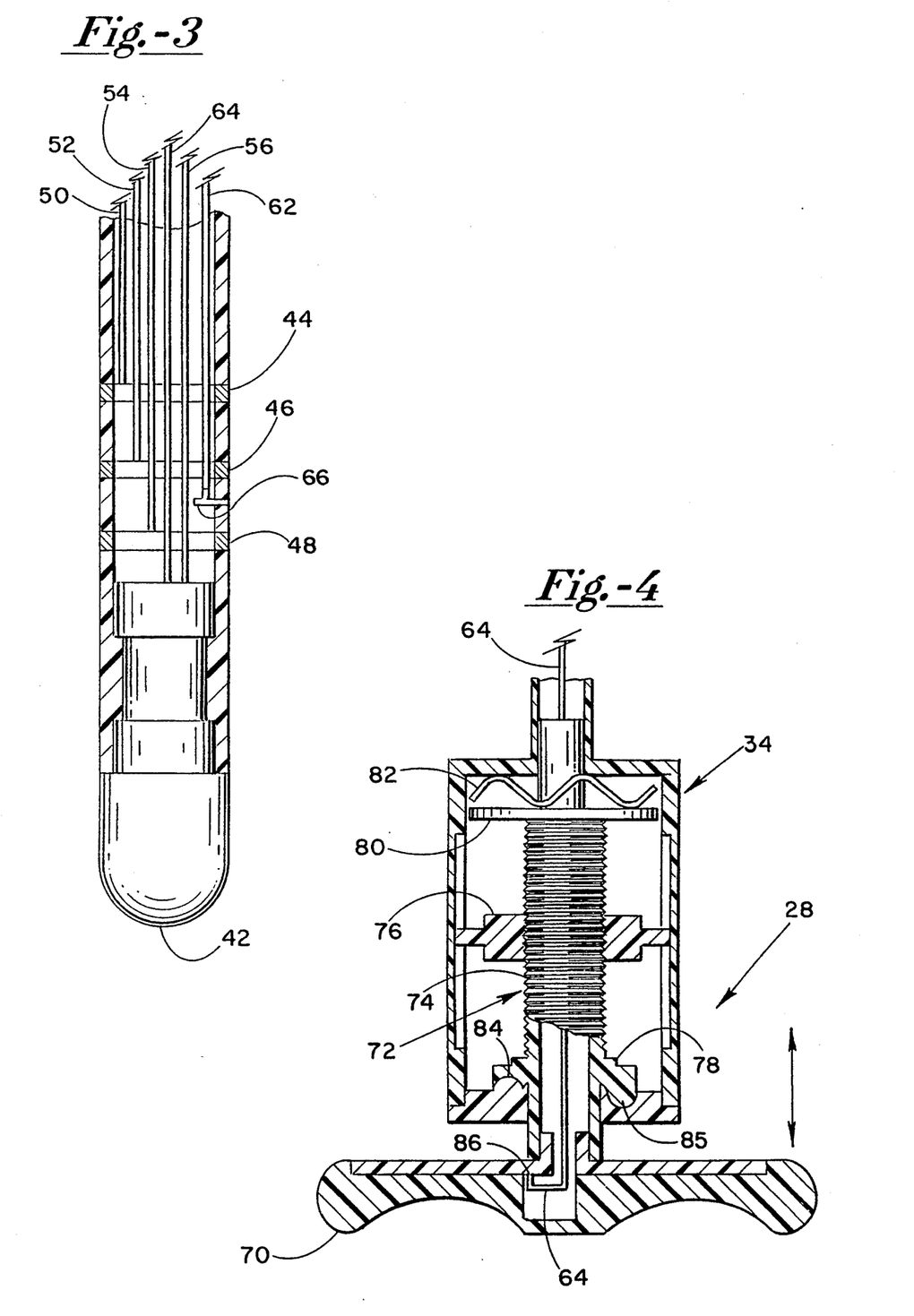
FIG. 3 is a further enlarged fragmentary view, with parts cut away, of the tip section of the catheter.
FIG. 4 is an enlarged view, partially in section, of the hand-operated, lateral tip deflection control knob.

As shown, enlarged for greater clarity in FIGS. 2 and 3, the catheter tip system 42 includes a plurality of electrodes 44, 46 and 48 which are in electrical communication with the external environment of the tip and with respective insulated electrical conductors 50, 52 and 54. The conductors are threaded through the catheter tubes 40 and 12 and the handle to separate pick-offs on the jack 16. The ablation electrode 42 may be adapted to be connected as input to a recording system in a mapping mode or as output from a source of high frequency electrical power via conductor or conductors 56, when operated in an ablating mode, as desired.

The lateral tip deflection is achieved by high torque wire 64 which is connected to the tip electrode at the distal end and threaded through the central core of the catheter tubing and proximally through the tubing 32 to the lateral control knob 28. A vertical tip deflection control wire 62 is inserted into the deflectable portion of the catheter in an off-center position and has a distal extremity anchored to the catheter side wall by a T-shaped stainless steel pin 66 just below the tip electrode. The vertical deflection control wire 62 is threaded through the central lumen of the catheter to the handle 10 and the proximal end anchored to the movable portion of the handle 18. Sliding the handle member 18 on the shaft portion thereby results in vertical deflection changes of the flexible catheter tip.

The hand-operated rotatable lateral tip deflection control knob system is more fully described in relation to the enlarged view of FIG. 4. The hand-operated knob system 28 includes an outer cylindrical member 34, a finger-operated bidirectional adjustable knob member 70, connected to an internal cylinder 72 having a series of threads 74 and a rotating ring with threads 76. The ring 76 rides the main shaft and it is limited in the number of rotations by the lower shoulder 78 and upper limit stopper 80. A spring 82 pushes the knob member upward with respect to the handle 70 engaging the locking spline at 84 and 85. The control wire 64 traverses the knob system and is anchored on the knob at 86 so that the rotational torque applied to the control wire 64 is directly controlled by the rotation of the knob 70.

While it will be appreciated that any mechanical equivalent set-up can be used which accomplishes the aims of the hand-operated rotatable knob control system 28, the one pictured in FIG. 4 operates basically in the following manner. The knob 70, together with the attached internal cylinder 72, is reciprocally adjustable in the longitudinal direction against the return spring 82 such that when the handle 70 is pushed in, the rounds and sockets 84 and 85 disengage, allowing the threaded rod or cylinder 72 to be rotated with respect to the member 76. The end of the wire 64 is fixed in position in the knob 70 at 86 such that rotation of the knob 70 applies a rotational torque in the desired direction to the control wire 64, which is, in turn, transmitted to the tip 42. The spring 82 normally maintains the rounds and sockets in a meshed position such that relative rotation is otherwise precluded thereby maintaining the rotational torque on the wire 64 constant. The rotation of the knob 70 is limited by stops 80, 84 and 85 to a desired number of turns such that the potential lateral force exerted by the catheter tip 42 is maintained below a level which could shear the wire off the catheter tip.

In operation, the catheter system is introduced by an incision into the femoral artery and routed through the vascular system into the desired chamber of the patient's heart. Once the proper chamber is reached, reciprocal movement of the handle 18, together with depression and rotation of the knob 70, produces precise control of intricate vertical and lateral movement of the tip member 42 such that any point on the wall of the chamber is readily accessible to the electrodes. The electrode members 44, 46 and 48 can be utilized to map the cardiac depolarization potentials throughout the chamber, thereby locating and mapping the early activation site. The tip electrode is used to transfer the energy for tissue ablation, and is used in a mapping mode.

Figure 5A:
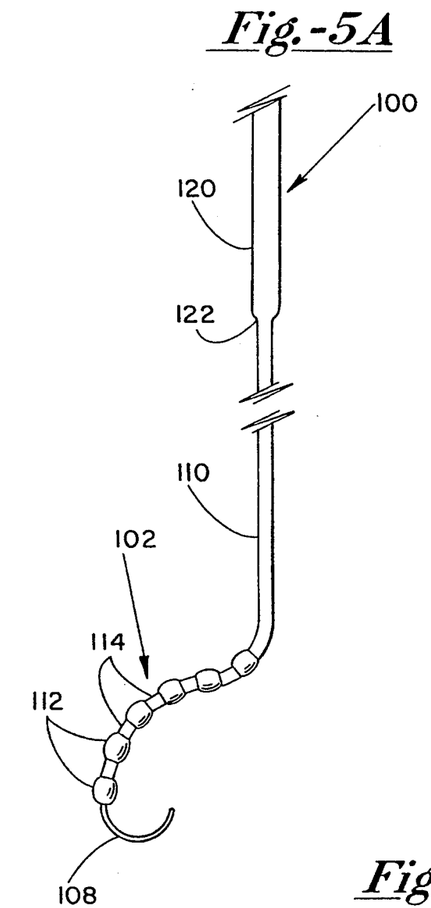
FIGS. 5A-5C show other embodiments of an electroded catheter tip of predetermined shape for the catheter system of the invention.
Figure 5B:
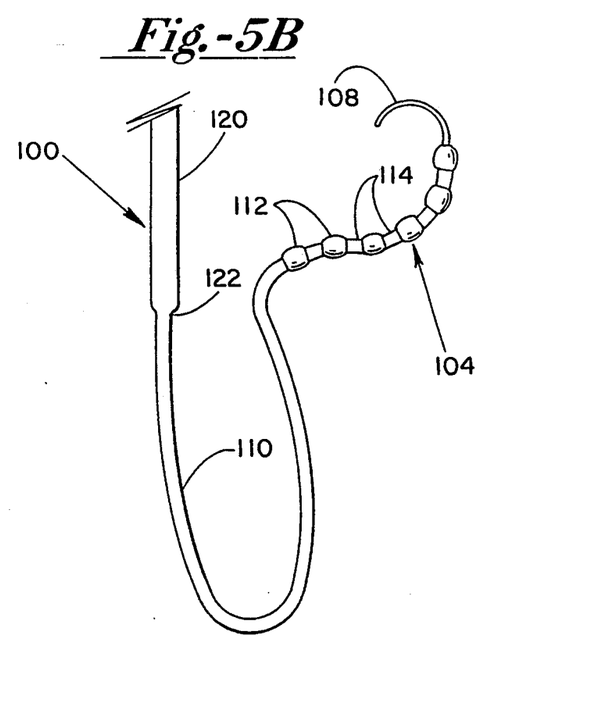
Figure 5C:
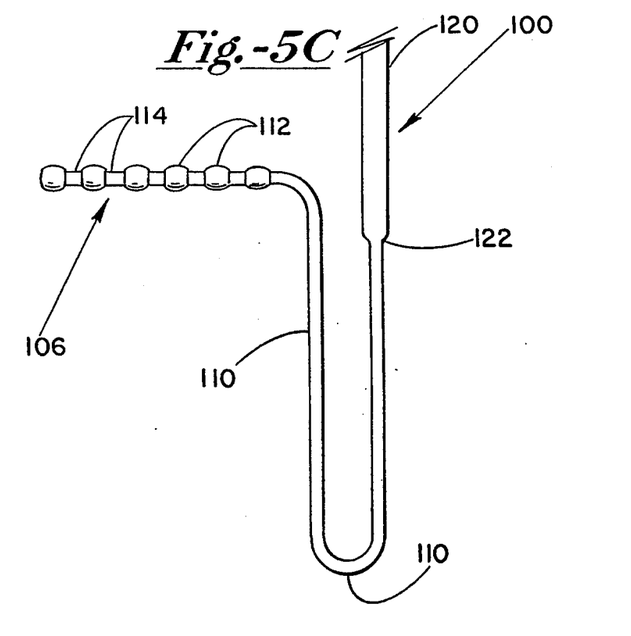

Of course, as shown in the FIGS. 5A–5C and 6, the catheter tip may be configured in any desired specialized shape to better address specific sites or internal cardiac areas. This may be accomplished by providing a variety of electroded catheter tip sections of predetermined fixed shapes as by using memoried materials such as metal alloys and plastics. An example of these is shown in FIGS. 5A and 5B in the form of a supra valvular mapping and ablation tip designed to address the atrial side of the A-V ring. The configuration of FIG. 5C is pre-shaped to address the ventricular side of the A-V ring. The catheter tip, generally at 100, includes a segment of one of several predisposed configurations such as those shown at 102, 104 and 106, having an approximate length of 4.2 cm (for a tip equipped with 6 4 mm ring electrodes with 3 mm spacing therebetween). A wire tail segment 108 which is about 2.0 cm in length and is included in FIGS. 5A and 5B aids in stabilizing precise placement of the electrodes. The catheter tip further contains a highly flexible proximal segment 110 which may be about 8.5 cm in length and operates to maneuver the pre-shaped portion. The electroded section includes individually connected and separately operable ring electrodes 112 separated by spaces 114. The electrodes may be of any convenient size and spacing.

FIG. 5C shows another specialized controlled shape for the tip 100 in which the side arm segment 106 is straight. This shape has been found useful in intravascular mapping and ablation at the ventricular side of the A-V ring and for accessing the posterior accessory pathways (AP) in its directed configuration and for use in addressing the left free wall AP in a right directed version. The remainder of the flexible tip section at 118 is similar to the flexible tip section 110 of FIGS. 5A and 5B and 40 of FIG. 2 being attached to the main catheter tube 120 as by a transition at 122.

The precision of the lateral displacement possible with the catheter system of the invention makes catheter-initiated ablation of tissue with respect to curing heart arrhythmias much easier and more precise. This makes the procedure less time-consuming and much more practical than with previous systems.

Figure 6:
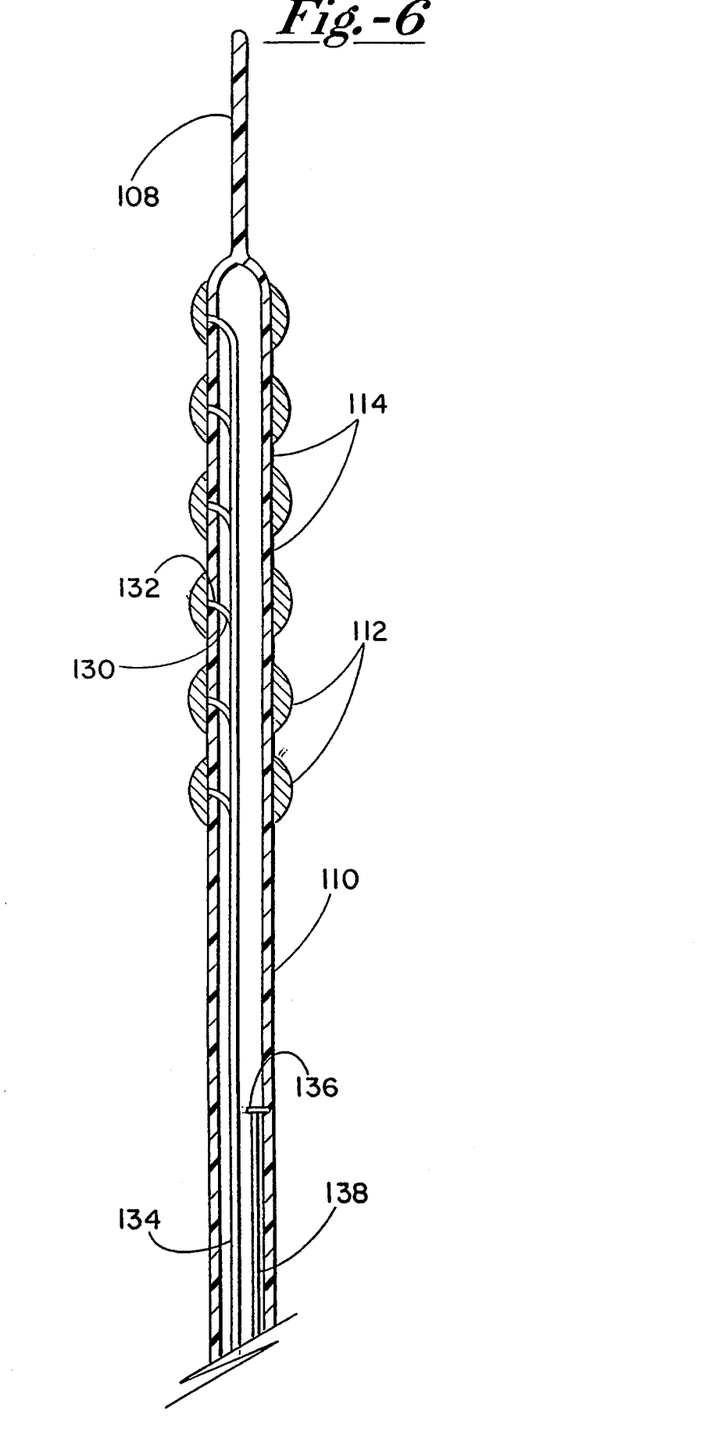
FIG. 6 represents an enlarged detailed view, partially in section, of an electroded mapping/ablation tip in accordance with FIGS. 5A-5C.

FIG. 6 details a typical electroded catheter tip with a plurality of ring electrodes 112 spaced laterally at 114. Each electrode is individually connected to an insulated conductor 130 as at 132. The conductors are bundled together as at 134 and are conveyed to controls outside the catheter in a well-known manner. A control pin 136 together with a control wire 138 are also provided for the flexible segment 110 to maneuver the devices as described above.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A deflectable catheter system for use in performing tissue mapping/ablation comprising:

(a) a central catheter comprising an elongated, flexible plastic tube having a proximal end and a distal end, having an outside diameter small enough to pass through an arterial vascular system from an introducer site, and further describing an internal lumen of a relatively large size extending from the proximal end to the distal end and having a tube wall providing stiffness required to enable routing of the catheter through the arterial vascular system;

(b) a relatively short flexible distal catheter section connected to the distal end of the central catheter comprising a flexible plastic tube having an electrode segment and having an external surface and terminating in a distal tip and having an outside diameter able to pass into any cardiac chamber, having a proximal and a distal end and further describing a continuous internal distal lumen extending from the proximal end to the distal end of the distal catheter section and having a flexible tube wall;

(c) electrode means for providing electrical connection with encountered surfaces of adjacent tissue comprising at least one electrode carried by said electrode segment of the distal catheter section connected through the catheter system and in communication with the external surface of the distal catheter section;

(d) an axial deflection control element threaded within the internal lumen and the distal lumen and having a distal end anchored at a point at or near the distal end of the distal catheter section in a manner such that the reciprocal movement of the axial deflection control element in the distal catheter section lumen deflects the distal tip of the distal catheter section in a plane substantially parallel the direction of element movement;

(e) means for longitudinally displacing the axial deflection control element along the distal lumen;

(f) a radial deflection control element threaded within lumen of the distal catheter section and having a distal end anchored at or near the distal tip of the distal catheter section in a manner such that the application of rotational torque to the radial deflection control element produces a corresponding deflection of the distal tip of the distal catheter section in a plane substantially parallel to the direction of the applied rotational torque; and (g) means fox applying the rotational torque to the radial deflection control element.

2. The apparatus of claim 31 wherein:

(a) the means for longitudinally displacing the axial deflection control element along the flexible distal catheter section further comprises:

(1) hand-operated control handle having longitudinally displaceable section attached to the axial deflection control element, the longitudinal motion of which causes a corresponding displacement of the axial deflection control element end thereby controls the axial deflection of the distal tip; and (b) wherein the means for applying the rotational torque to the radial deflection control element further comprises;

(1) a self-locking, hand-rotatable lateral adjustment control knob spaced from the control handle and attached to the radial deflection control element in a manner such that rotation of the knob left or right applies a corresponding rotational torque to the radial deflection control element which transmits it to the distal tip thereby causing the distal tip to deflect laterally as desired.

3. The apparatus of claim 2 wherein the axial control element and the radial control elements are wire elements.

4. The apparatus of claim 1 wherein the axial control element and the radial control elements are wire elements.

5. The apparatus of claim 4 wherein at least a portion of the distal catheter section is configured in a predetermined non-linear specialized shape, wherein the shape is resumed upon relaxed deployment of the distal section.

6. The apparatus of claim 5 further comprising a tail segment attached to or as a continuation of the distal tip of the distal catheter section to aid in positioning and stabilizing the electrode means.

7. The apparatus of claim 1 wherein the distal tip of the distal catheter section further comprises a plurality of spaced electrodes suitable for both mapping and ablation.

8. The apparatus of claim 1 wherein the electrode segment of the distal catheter section further comprises:
   (a) a plurality of mapping electrode means for receiving impulses indicative of electrical activity of internal cardiac tissue contacted by the distal tip of the distal catheter section;
   (b) a plurality ablation electrode means for receiving high frequency electrical current and supplying ablation energy to contacted tissue;
   (c) input/output means for receiving and transmitting electrical impulses connected to the mapping and ablation electrode means; and
   (d) connection means for connecting the input/output means.

9. The apparatus of claim 1 wherein the distal tip of the distal catheter section further comprises:
   a plurality of serially spaced mapping electrode means for receiving impulses indicative of electrical activity of internal cardiac tissue contacted by the distal tip of the distal catheter section;
   a plurality of serially spaced ablation electrode means for receiving high frequency electrical current and supplying ablation energy to contacted tissue;
   input/output means for receiving and transmitting electrical impulses connected to each of the mapping and ablation electrode means; and
   connection means for separately connecting the input/output to each said electrode means.

10. The apparatus of claim 1 wherein at least a portion of the distal catheter section is configured in a predetermined, non-linear specialized shape, wherein the shape is resumed upon deployment of the distal section.

11. The apparatus of claim 10 further comprising a tail segment attached to or as a continuation of the distal tip of the distal catheter section to aid in positioning and stabilizing the electrode means.

12. A method of mapping cardiac electrical activity and ablating cardiac tissue comprising the steps of:
   (a) introducing a deflectable cardiac mapping and ablation catheter system into a vascular system of a patient, the system comprising:
      (1) a catheter including a highly flexible tubular distal catheter section for entering and navigating throughout any cardiac chamber and having a distal tip segment carrying a mapping and ablation electrode system;
      (2) a multi-element control means for enabling and controlling the movement of the distal catheter section in any direction in a manner such that the distal tip is capable of accessing any point on the wall of the chamber entered; and
      (3) wherein the multi-element control means further includes:
         (i) an axial deflection control element connected to the distal tip segment and operable to deflect the distal tip segment of the catheter section in a controlled manner in a plane substantially parallel to the longitudinal axis of the tubular catheter,
         (ii) a lateral deflection control element connected to the tip segment and operable to deflect the distal tip segment of the catheter section in a controlled manner in a plane substantially perpendicular to the longitudinal axis of the tubular catheter;
   (b) adjusting tension in the axial deflection control element and the lateral deflection control element to deflect and steer the tip electrode system to access the tissue surface of the chamber as required;
   (c) operating the tip electrode system to map cardiac electrical activity; and
   (d) operating the tip electrode system to ablate early activation sites as indicated.

13. The method of claim 12 wherein the distal tip segment of the flexible tubular distal catheter section is configured in a predetermined specialized shape wherein the shape is resumed upon deployment of the distal catheter section and further comprising the step of maneuvering the predetermined shape to map the tissue surface of specifically designated cardiac areas.

14. A mapping and ablation catheter comprising:
   (a) an elongated flexible tubular section having a distal end and a readily flexible tubular distal catheter section attached to said distal end for entering and navigating throughout any cardiac chamber having a longitudinal axis parallel to the length thereof and having a distal tip the distal catheter section having electrode means for mapping and ablating;
   (b) a dual-element biplanar control means for enabling and controlling the movement of the distal catheter section in any direction in a manner such that the distal tip is capable of accessing any point on a surface of the chamber entered; and
   (c) wherein the dual-element biplanar control means further includes;
      (1) an axial deflection control element connected to the distal tip and operable to deflect the distal tip of the distal catheter section in a controlled manner in a plane substantially parallel to the longitudinal axis of the tubular section,
      (2) a radial deflection control element connected to the distal tip end operable independent of any rotation of the catheter itself and responsive to applied rotational torque to deflect the distal tip of the distal catheter section in a controlled manner in a plane substantially perpendicular to the longitudinal axis of the tubular section.

15. A mapping and ablation catheter comprising:
   (a) an elongated flexible tubular section having a distal end and a readily flexible tubular distal catheter section attached to said distal end for entering and navigating throughout any cardiac chamber having a longitudinal axis parallel to the length thereof and having a distal tip;

(b) a dual-element biplanar control means for enabling and controlling the movement of the distal catheter section in any direction in a manner such that the distal tip is capable of accessing any point on a surface of the chamber entered; and (c) wherein the dual-element biplanar control means further includes:

(1) an axial deflection control element connected to the distal tip and operable to deflect the distal tip of the distal catheter section in a controlled manner in a plane substantially parallel to the longitudinal axis of the tubular section, (2) a radial deflection control element connected to the distal tip end operable independent of any rotation of the catheter itself and responsive to applied rotational torque to deflect the distal tip of the distal catheter section in a controlled manner in a plane substantially perpendicular to the longitudinal axis of the tubular section; and (d) electrode means for providing electrical connection with encountered surfaces of adjacent tissue, said electrode means being carried by the tubular distal catheter section near or at the distal tip.

16. The apparatus of claim 15 wherein the electrode means further comprises:

(a) a plurality of serially spaced electrodes capable of optionally functioning to map electrical activity and to ablate contacted tissue; and (b) separate conductor means connected to each of said plurality of serially spaced electrodes for optionally receiving and transmitting electrical impulses thereby enabling individual input/output interface with each said plurality of serially spaced electrodes.

17. The apparatus of claim 16 wherein at least a portion of the distal catheter section is configured in a predetermined, nonlinear shape, wherein the shape is resumed Upon relaxed deployment of the distal catheter section.

18. The apparatus of claim 17 further comprising a tail segment attached to or as a continuation of the distal tip of the distal catheter section to aid in positioning and stabilizing the position 0f the electrode means.

19. The apparatus of claim 15 further comprising a tail segment attached to or as a continuation of the distal tip of the distal catheter section to aid in positioning and stabilizing the position of the electrode means.

20. A mapping and ablation catheter comprising:

(a) an elongated flexible tubular section having a distal end and a readily flexible tubular distal catheter section attached to said distal end for entering and navigating throughout any cardiac chamber having a longitudinal axis parallel to the length thereof and having a distal tip the distal catheter section having electrode means for mapping and ablating;

(b) a dual-element biplanar control means for enabling and controlling the movement of the distal catheter section in any direction in a manner such that the distal tip is capable of accessing any point on a surface of the chamber entered; and (c) wherein the dual-element biplanar control means further include:

(1) an axial deflection control element connected to the distal tip and operable to deflect the distal tip of the distal catheter section in a controlled manner in a plane substantially parallel to the longitudinal axis of the tubular section, (2) a radial deflection control element connected to the distal tip end operable independent of any rotation of the catheter itself and responsive to applied rotational torque to deflect the distal tip of the distal catheter section in a controlled manner in a plane substantially perpendicular to the longitudinal axis of the tubular sectional; and (d) wherein at least a portion of the distal catheter section is configured in a predetermined, non-linear shape, wherein the shape is resumed upon relaxed deployment of the distal catheter section.

* * * * *

UNITED STATES PATENT AND TRADEMARK OFFICE
CERTIFICATE OF CORRECTION

PATENT NO. : 5 354 297
DATED : October 11, 1994
INVENTOR(S) : Boaz Avitall

It is certified that error appears in the above-indentified patent and that said Letters Patent is hereby corrected as shown below:

In column 8, line 31, delete "the" (First Occurrence).

In column 8, line 47, delete "fox" and insert -- for -- .

In column 8, line 49, delete "31" and insert -- 1 -- .

In column 9, line 68, before "electrode", insert -- tip -- .

In column 11, line 40, delete "Upon" and insert -- upon -- .

In column 12, line 4, delete "Of" and insert -- of -- .

In column 12, line 24, delete "include" and insert -- includes --

Signed and Sealed this

Thirteenth Day of December, 1994

Attest:

BRUCE LEHMAN

*Attesting Officer*    *Commissioner of Patents and Trademarks*